United States Patent
Kim et al.

(10) Patent No.: US 9,582,880 B2
(45) Date of Patent: Feb. 28, 2017

(54) AUTOMATED IMAGE SYSTEM FOR SCORING CHANGES IN QUANTITATIVE INTERSTITIAL LUNG DISEASE

(71) Applicant: THE REGENTS OF THE UNIVERSITY OF CALIFORNIA, Oakland, CA (US)

(72) Inventors: Hyun J. Kim, Porter Ranch, CA (US); Jonathan G. Goldin, Los Angeles, CA (US); Matthew S. Brown, Marina del Rey, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 10 days.

(21) Appl. No.: 14/708,949

(22) Filed: May 11, 2015

(65) Prior Publication Data
US 2015/0324982 A1 Nov. 12, 2015

Related U.S. Application Data

(63) Continuation of application No. PCT/US2013/069501, filed on Nov. 11, 2013.
(Continued)

(51) Int. Cl.
*G06K 9/00* (2006.01)
*G06T 7/00* (2006.01)
(Continued)

(52) U.S. Cl.
CPC .............. *G06T 7/0014* (2013.01); *A61B 6/03* (2013.01); *A61B 6/032* (2013.01); *A61B 6/5217* (2013.01);
(Continued)

(58) Field of Classification Search
CPC ......... A61B 6/00; A61B 6/032; A61B 6/5217; A61B 6/03; A61B 6/5258; A61B 6/50; G06T 7/0014; G06T 2207/10081; G06T 2207/20076; G06T 2207/20081; G06T 2207/30061
(Continued)

(56) References Cited

U.S. PATENT DOCUMENTS 6,011,862 A 1/2000 Doi et al.
6,058,322 A 5/2000 Nishikawa et al.
(Continued)

FOREIGN PATENT DOCUMENTS

KR 10-2012-0041468 A 5/2012

OTHER PUBLICATIONS

Korean Intellectual Property Office (KIPO), International Search Report and Written Opinion, PCT International Appln. No. PCT/US2013/069501, issued Feb. 27, 2014, pp. 1-10, with claims searched, pp. 11-15, corresponding to U.S. Appl. No. 14/708,949 herein.

*Primary Examiner* — Ali Bayat
(74) *Attorney, Agent, or Firm* — O'Banion & Ritchey LLP; John P. O'Banion

(57) ABSTRACT

Automated image analysis systems and methods are disclosed to quantify change in fibrosis and interstitial lung disease. The system generates scoring changes in Quantitative Interstitial Lung Disease (QILD) by filtering the uploaded images to minimize cross-site variability within images, sampling from a grid of pixels or voxels within the CT images, classifying individual pixels or voxels within downloaded images based on one or more selected texture features, generating a QILD score for each image based on
(Continued)

selected features within the image, and calculating a transition between QILD scores within the plurality of CT images.

26 Claims, 6 Drawing Sheets

Related U.S. Application Data

(60) Provisional application No. 61/725,015, filed on Nov. 11, 2011.

(51) Int. Cl.
*A61B 6/03* (2006.01)
*A61B 6/00* (2006.01)

(52) U.S. Cl.
CPC .... *A61B 6/5258* (2013.01); *G06T 2207/10081* (2013.01); *G06T 2207/20076* (2013.01); *G06T 2207/20081* (2013.01); *G06T 2207/30061* (2013.01)

(58) Field of Classification Search
USPC .......................................................... 382/131
See application file for complete search history.

(56) References Cited

U.S. PATENT DOCUMENTS

| | | | |
|---|---|---|---|
| 2003/0103665 A1* | 6/2003 | Uppaluri | ............... G06T 7/0012 382/131 |
| 2006/0018524 A1 | 1/2006 | Suzuki et al. | |
| 2015/0086483 A1* | 3/2015 | Porter | ................... A61B 6/032 424/9.2 |

* cited by examiner

AUTOMATED IMAGE SYSTEM FOR SCORING CHANGES IN QUANTITATIVE INTERSTITIAL LUNG DISEASE

CROSS-REFERENCE TO RELATED APPLICATIONS

This application is a 35 U.S.C. §111(a) continuation of PCT international application number PCT/US2013/069501 filed on Nov. 11, 2013, incorporated herein by reference in its entirety, which claims priority to, and the benefit of, U.S. provisional patent application Ser. No. 61/725,015 filed on Nov. 11, 2012, incorporated herein by reference in its entirety. Priority is claimed to each of the foregoing applications.

STATEMENT REGARDING FEDERALLY SPONSORED RESEARCH OR DEVELOPMENT

This invention was made with Government support under HL060587 and HL072424, awarded by the National Institutes of Health. The Government has certain rights in the invention.

The above-referenced PCT international application was published as PCT International Publication No. WO 2014/075017 on May 15, 2014, which publication is incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to diagnostic imaging, and more particularly to automated Computer Aided Diagnosis (CAD) scoring system and methods.

2. Description of Related Art

Increasing evidence is found that in patients with idiopathic pulmonary fibrosis (IPF) and scleroderma, the extent of interstitial lung disease is an important predictor of prognosis. The median survival of IPF patients is 2-5 years. Visual semi-quantitative scoring is a current standard to evaluate the disease. However, semi-quantitative scoring systems are limited by the requirement of expert radiologists and by moderate inter-observer variation so they tend to be unreliable for assessing change in disease status. To date, all prospective trials use a visual radiologist score, in terms of worsening or not-worsening in disease pattern.

BRIEF SUMMARY OF THE INVENTION

Systems and methods are disclosed for generating Quantitative Interstitial Lung Disease (QILD) scores for estimating a transitional change in the multi-levels of fibrotic reticulation, ground glass and normal patterns. The transitional score of change is a sensitive metric for testing treatment efficacy in QILD. The systems and methods have commercial application in patient care and clinical trials for prognosis of patient status and/or improvement over time in fibrosis score, interstitial disease score or transitional score, depending upon the mechanism of treatment.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

The description below details a system and method to calculate interstitial lung disease quantitative metrics using a combination of texture features from a de-noising technique, robust feature selection, classification model, and the artificial intelligence of computer-aided diagnosis. It includes a de-noising technique as part of a filter in multi-center trials to reduce variability across sites.

1. Imaging Method Overview

Figure 1:
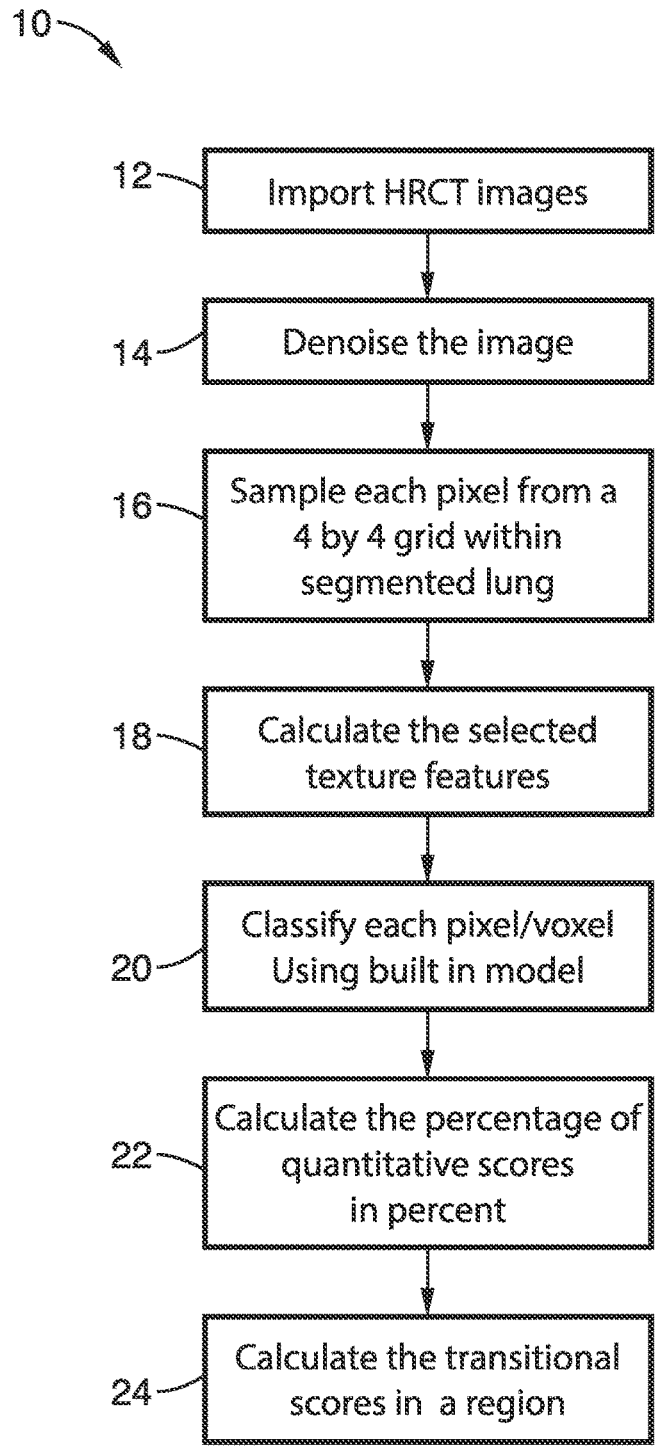
FIG. 1 is a schematic flow diagram of an automated image method for scoring changes in Quantitative Interstitial Lung Disease (QILD) in accordance with the present invention.

FIG. 1 shows a high-level schematic flow diagram of an automated image method 10 for scoring changes in Quantitative Interstitial Lung Disease (QILD) in accordance with the present invention.

Figure 2A:
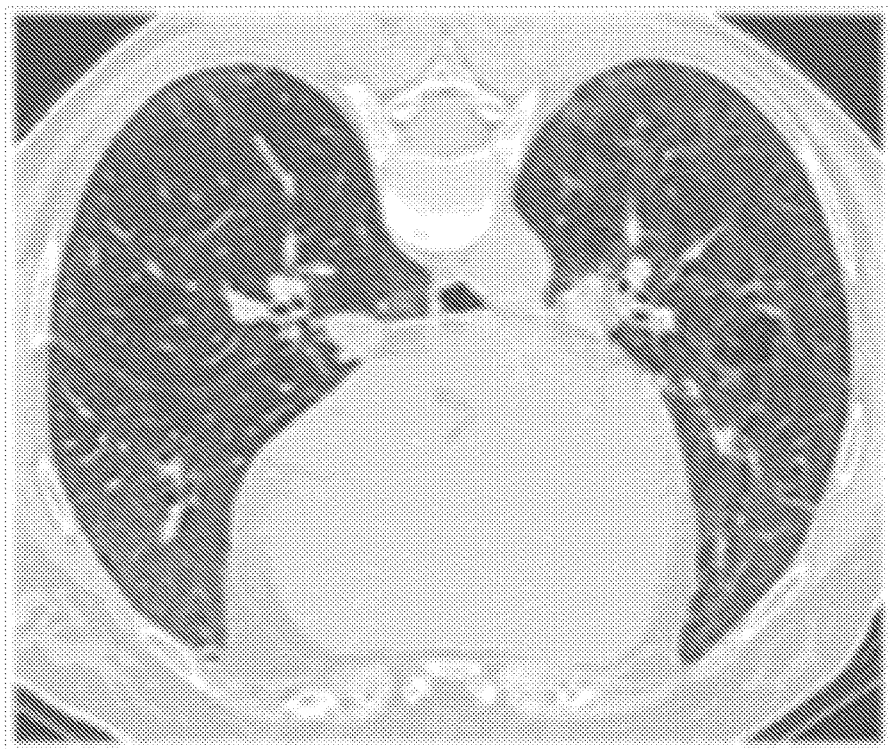
FIG. 2A shows an imported HRCT image in accordance with the present invention.

At step 12, High Resolution Computed Tomography (HRCT) images, such as that shown in FIG. 2A, are imported or loaded.

At step 14, a de-noise algorithm 14 is applied to the uploaded image, which may be implemented as a filter in multi-center trials to reduce variability across sites. Next, each pixel is sampled from a grid (e.g. 4×4) within the segmented lung at step 16. Selected texture features are then calculated at step 18, and each pixel/voxel is classified at step 20. The percentage of calculated scores is then calculated at step 22. Finally, the transitional scores in a region are calculated at step 24.

2. De-Noise Algorithm

Step 12 may be implemented as a filter in multi-center trials to reduce variability across sites, and includes a de-noise algorithm incorporating Gilles' algorithm and an extension of Aujol's Algorithm as follows:

1) Initialization:

$$u_0 = v_0 = 0 \quad \text{Eq. 1}$$

2) Iterations:

$$w_{n+1} = P_{\delta B_G}(f - u_n - v_n) \quad \text{Eq. 2}$$

$$v_{n+1} = P_{\mu B_G}(f - u_n - w_{n+1}) \quad \text{Eq. 3}$$

$$u_{n+1} = f - v_{n+1} - w_{n+1} - P_{\lambda B_G}(f - v_{n+1} - w_{n+1}) \quad \text{Eq. 4}$$

3) Stopping test: we stop if $$\max(|u_{n+1} - u_n|, |v_{n+1} - v_n|, |w_{n+1}|) \le \epsilon, \quad \text{Eq. 5}$$

where u, v and w represents the geometric, texture, and noised images, respectively. The sum of the u and v images is the de-noised image. $P_{B_G}$ is a non-linear projection, $\delta$ represents the amount of noise and $\lambda$ represents the accuracy of the algorithm. The sum of u, v, and w is approximately equal to the original CT image if the algorithm converges. The de-noise algorithm initializes according to Eq. 1 and iterates according to Eq. 2, Eq. 3, and Eq. 4. The algorithm stops according to Eq. 5.

In the present example, for the sake of simplicity and consistency, we set the noise parameter ($\delta$) at 50 and texture parameter ($\mu$) at 450, which were the upper bound of the standard deviation in aorta and in CT image across patients. Because the parameter has a certain threshold, the results of de-noised images are similar to the values above the threshold. The residual parameter ($\lambda$) was set to 1, which controls the convergence of the algorithm.

Any computerized image can be digitalized into N by N vectors, where each element of a matrix is a pixel. We denote X by Euclidian space $R^{N \times N}$ and denote $Y = X \times X$. In a CT image, the window size is 512 by 512.

Each element of the projection matrix P is solved by a fixed point method according to Eq. 6 and Eq. 7 below:

$$p^0 = 0 \text{ and} \quad \text{Eq. 6}$$

$$p_{i,j}^{n+1} = \frac{p_{i,j}^n + \tau(\nabla(\text{div}(p^n) - f/\lambda))_{i,j}}{1 + \tau|(\nabla(\text{div}(p^n) - f/\lambda))_{i,j}|} \quad \text{Eq. 7}$$

Theoretically, this projection converges at $\tau \le \frac{1}{8}$. Practically, $\frac{1}{4}$ is used.

Defining a discrete total variation, a discrete version of the gradient operator is used. If $u \in X$, the gradient $\nabla u$ is a vector in Y given by:

$$(\nabla u)_{i,j} = ((\nabla u)_{i,j}^1, (\nabla u)_{i,j}^2).$$

The gradient operator is found using:

$$(\nabla u)_{i,j}^1 = \begin{cases} u_{i+1,j} - u_{i,j} & \text{if } i < N \\ 0 & \text{if } i = N \end{cases} \quad \text{Eq. 8}$$

and $$(\nabla u)_{i,j}^2 = \begin{cases} u_{i,j+1} - u_{i,j} & \text{if } j < N \\ 0 & \text{if } i = N \end{cases}, \quad \text{Eq. 9}$$

The divergence operator is found by analogy with the continuous setting by $\text{div} = -\nabla^*$, where $\nabla^*$ is the adjoint of $\nabla$: that is, for every $p \in Y$, and $u \in X$, $(-\text{div } p, u)_x = (p, \nabla u)_Y$ to get Eq. 10:

$$(\text{div}(p))_{i,j} = \quad \text{Eq. 10}$$

$$\begin{cases} p_{i,j}^1 - p_{i-1,j}^1 & \text{if } 1 < i < N \\ p_{i,j}^1 & \text{if } i = 1 \\ -p_{i-1,j}^1 & \text{if } i = N \end{cases} + \begin{cases} p_{i,j}^2 - p_{i,j-1}^2 & \text{if } 1 < j < N \\ p_{i,j}^2 & \text{if } j = 1 \\ -p_{i,j-1}^2 & \text{if } j = N \end{cases}$$

Figure 2B:
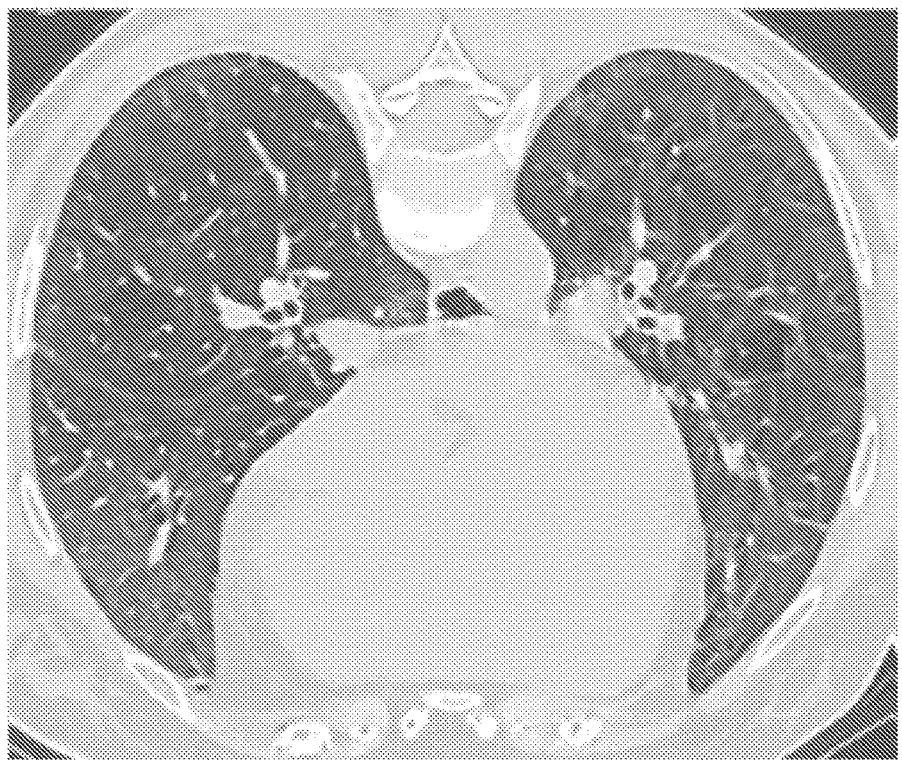
FIG. 2B shows the imported HRCT image of FIG. 2A after application of the de-noise algorithm in accordance with the present invention.

FIG. 2B shows and exemplary imported HRCT image after application of the de-noise algorithm 12.

3. Grid Sampling

Figure 2C:
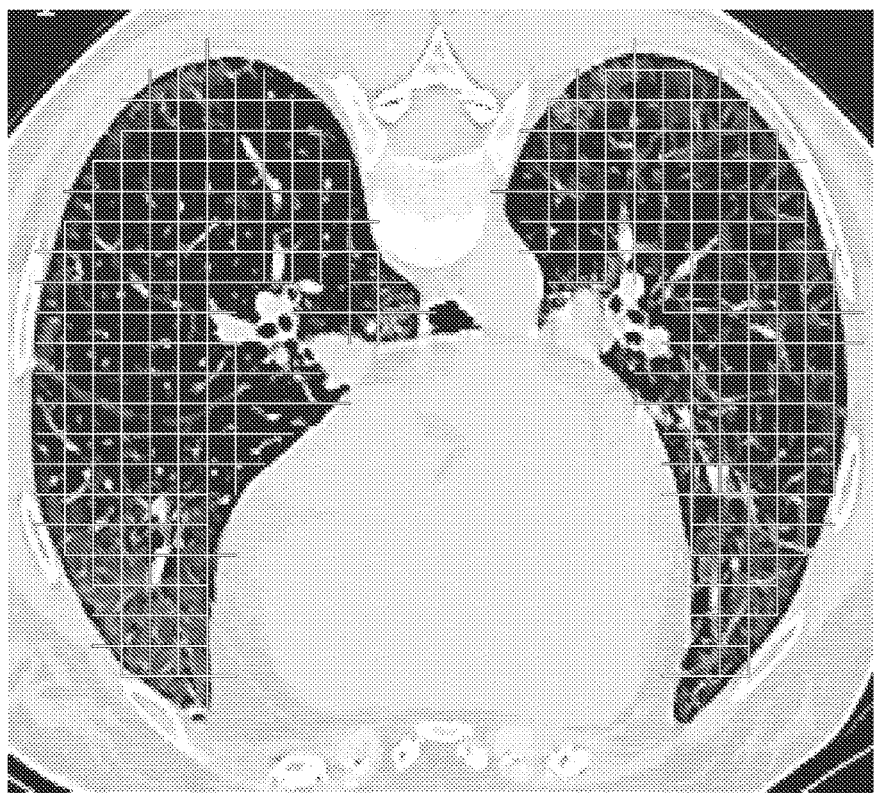
FIG. 2C shows the image of FIG. 2B after application of the grid-sampling step in accordance with the present invention.

To improve efficiency of computing and minimize the redundant information due to spatial correlation, a grid sampling technique is employed at step 14. A 4×4 grid was chosen, however, other grid patterns are contemplated. In the present configuration, one pixel out of sixteen pixels is chosen. Considering repeatability, a set location of the second row and third column in the 4×4 grid was chosen. FIG. 2C shows the de-noised image after application of the grid-sampling step 16.

4. Texture Feature Calculation

Referring now to texture feature selection and calculation step 18, texture differences can be used as key components to distinguish disease patterns in lung. In a chosen location from the grid, texture features can be derived in 12 by 12 neighboring of a pixel using available statistical and structural approaches available in the art.

In summary, 9 statistical features, 27 texture features from co-occurrence matrix, and 20 acquisition length texture features were used. A summary of the textural features is listed in Table 1.

Due to the high-dimensional features, selecting important features is critical. In a preferred embodiment, the method implemented in step 18 is based on variable selection via non-concave penalized likelihood and its oracle properties. This approach demonstrates excellent statistical properties in simultaneous variable selection and estimation in order to reduce stochastic errors with the usage of smoothly clipped absolute deviation penalty (SACD) function, which provide sparsity in variable selection. The penalized likelihood is defined as $$Q(\beta) = \text{Liklihood function}(\beta) - \text{SCAD penalty function } (\beta, \lambda).$$

To obtain a penalized maximum likelihood estimator of $\beta$, we minimized $-Q(\beta)$ with respect to p $\beta$ for some thresholding parameter $\lambda$. For example, we set a parameter of a disease type of interest among reticular pattern or ground glass as (i.e. $y_i=1$) or not ($y_i=0$), thus the likelihood follows a Bernoulli distribution with success probability. The variable selection for logistic regression can be achieved by maximizing the penalized likelihood function.

5. Classification Model

Referring now to classification step 20, a classifier model was built using Support Vector Machine (SVM) programming. SVM has been demonstrated to have excellent performance in hand digit recognition, pattern recognition, and interstitial lung disease. The basic concept of SVM is to find support vectors that maximize the margin between classes. In maximizing the margin, kernel (shape of separating hyper-plane) and cost of misclassification need to be pre-determined before classification. Here, our cases performed best using radial basis function with cost 1 from selected texture features by the penalized likelihood model. Based on support vectors from selected features in the training set, the training and testing set were classified as multi-categorical disease types. The overall pixel classification rate, sensitivities, and specificities by each category were reported.

Table 2 shows the training set of classification results using texture features from the de-noised image with non-concave penalized likelihood variable selection and a support vector machine (SVM) classifier for the patterns: Fibrotic Reticulation (FR), Ground Glass (GG), and Normal (NL). For the normal (NL) pattern, 339 pixels in a normal lung from a scleroderma lung study, and 5991 pixels in airways, major and minor fissures, hieum large vessels, and small parenchyma vessels from a lung image database consortium were included.

Table 3 shows a test set of classification results using texture features from de-noised with nonconcave penalized likelihood variable selection and support vector machine classifier for Three Patterns: FR, GG, NL. For the normal (NL) pattern, 336 pixels in a normal lung from a scleroderma lung study and 5638 pixels in airways, major and minor fissures, hieum large vessels, and small parenchyma vessels from a lung image database consortium were included.

Classification rates for the training set and test set are provided in Table 4 and Table 5, respectively.

Figure 2D:
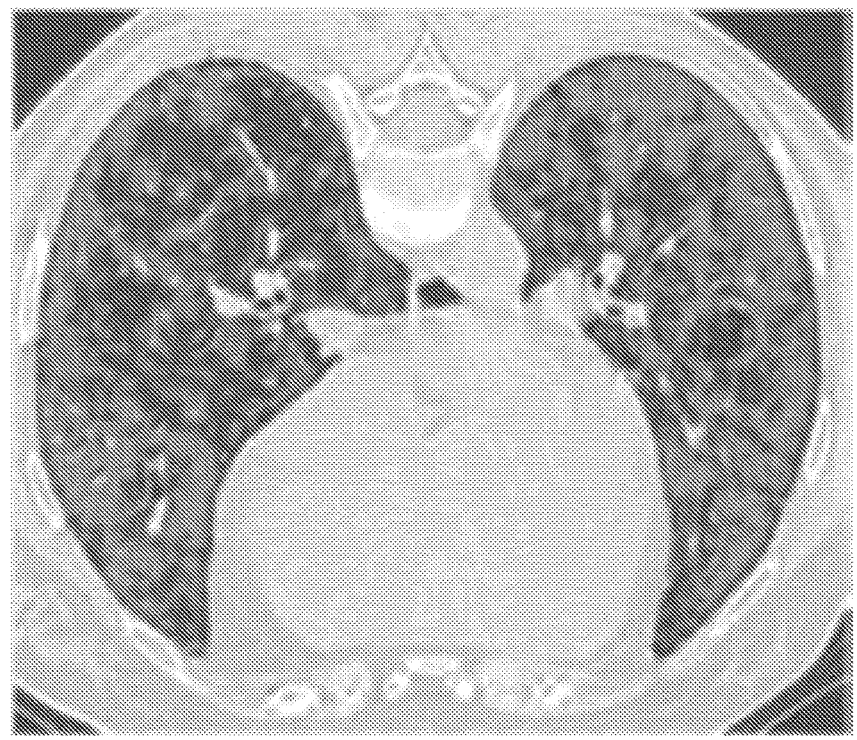
FIG. 2D shows the image of FIG. 2C after application of the classification model in accordance with the present invention.

FIG. 2D shows the image of FIG. 2C after application of the classification model in accordance with the present invention. In the image, 1=fibrotic reticulation or ground glass (lighter region s), 0=not interstitial disease.

6. Transitional Score

Referring now to step 22, the proportion of disease in a given region is set as a quantitative value using a fraction, where the numerator is the total number of pixels that are classified as a disease type (e.g. counts of all Interstitial Lung Disease), and the denominator is the total number (counts) of grid samples in the region. The disease types are quantitative fibrotic reticulation (QFR), quantitative ground glass (QGG) and quantitative normal patterns (QNL). The sum of QFR and QGG reflects the overall quantitative interstitial lung disease burden (QILD) [i.e. QILD score=QFR+QGG].

Referring to step 24, the change in the QILD score is equivalent to detecting changes in normal and abnormal patterns in a given region. However, the change in QILD may not be sensitive to find the changes within the interstitial disease patterns, i.e. from QGG to QFR. Disease progression and ILD often occurs in transition of QGG to QFR. Therefore, this may be a sensitive early indicator of disease progression or therapeutic response. Increasing ground glass can be interpreted into two ways: (a) if the quantitative normal pattern is reduced, it is assumed that the patient got worse; (b) if the quantitative fibrotic pattern is reduced, it is assumed that the patient got better. Reduction in ground glass can be interpreted similarly.

Calculation of the transitional score of hierarchical changes in accordance with the step 24 may be performed according to the following routine:

Transitional Score in an individual subject:
Initialization: Transitional Score=Changes in QILD score
  Indicating effective treatment
    If changes in QILD score<0 (meaning reduction in the interstitial component),
    Replace Transitional Score=Changes in QILD score+changes in QRF
  Indicating ineffective treatment
    (Meaning increase in the interstitial component and some portion of ground glass component changed into reticular pattern). If changes in QILD score>0 and changes in QGG<0, Update Transitional Score=Changes in QILD score−changes in QGG.
    (Meaning increase in the interstitial component and some portion of ground glass component changed into reticular pattern and the normal pattern also changed into ground glass, such that changes of ground glass is positive). If changes in QILD score>0 and changes in QGG>0, Update Transitional Score=Changes in QILD score+changes in QGG Transitional Score in Treatment group: estimating overall changes by treatment group
  A disease type of decomposition of Markov Decision Processes (MDP) is a partitioning.
  Π={Fibrotic Retiuculation, Gound Glass, Normal} of State S.
  Probability of changing a status of fibrotic reticulation (FR) to ground glass (GG) when a patient is treated with treatment A [notation Transition (FR, A, GG)=$p_A$, where $p_A$ is a probability between 0 and 1].

In a preferred embodiment, a Markov Chain Transition Matrix (MCTM) can be applied to estimate the changes in multi-disease patterns. The size of transitional matrix (Eq. 11) is a 3 by 3 per a region of interest, representing the fibrotic reticulation, ground glass, and normal:

$$P = \begin{bmatrix} P_{NL,NL} & P_{NL,GG} & P_{NL,FR} \\ P_{GG,NL} & P_{GG,GG} & P_{GG,FR} \\ P_{FR,NL} & P_{FR,GG} & P_{FR,FR} \end{bmatrix} \qquad \text{Eq. 11}$$

In the first row, the first element ($p_{NL, NL}$) is the probability of changing from normal to normal pattern; the second column ($p_{NL, GG}$) is the probability to change from normal to ground glass; the third column (p NL, FR) is the probability to change from normal to fibrotic reticulation. Similarly, the second and third rows are the probability to change from ground glass and fibrotic reticulation including honeycomb, respectively. In detail, the equation of MCTM is written in Table 3, where $QNL_1$, $QGG_1$, and $QFR_1$ are quantitative normal lung, quantitative ground glass, and quantitative fibrotic reticulation at baseline or the 1st measurement. Similarly $QNL_2$, QGG2, and $QFR_2$ are scores at the follow-up or the second measurement.

The equation of transitional score is defined by Eq. 12 and Eq. 13:

$$X^{(2)T} = P^T x^{(1)} \quad \text{Eq. 12}$$

$$X^{(2)T} = (QNL, QGG, QFR) \quad \text{Eq. 13}$$

Eq. 13 is a 3 by 1 vector at the follow-up score of normal lung patterns, ground glass, and reticular plus honeycomb patterns. $P^T$ is the transposed of 3 by 3 matrix listed above. $x^{(1)}$ is a 3 by 1 vector at the baseline score of normal lung patterns, ground glass, and reticular patterns.

For each pattern, the probability of being stable in the next visit is recorded in the diagonal term. The increment in good patterns is the transition probability of lower triangle (i.e. the elements below diagonal). The increment in worsening patterns is the transition probability of the upper triangle (the elements above diagonal). Each subject's baseline and follow-up can be written as MCTM and the summary statistics of probability in MCTM is reported to represent the changes over time in the three patterns.

Application of the MCMT probabilities may be extended to finite space of multiclass disease pattern. The probabilities can be estimated using Kolmogorov's forward equations and can be exploited to map transition rates and probabilities from probability data in multistate models.

7. Imaging System

Figure 3:
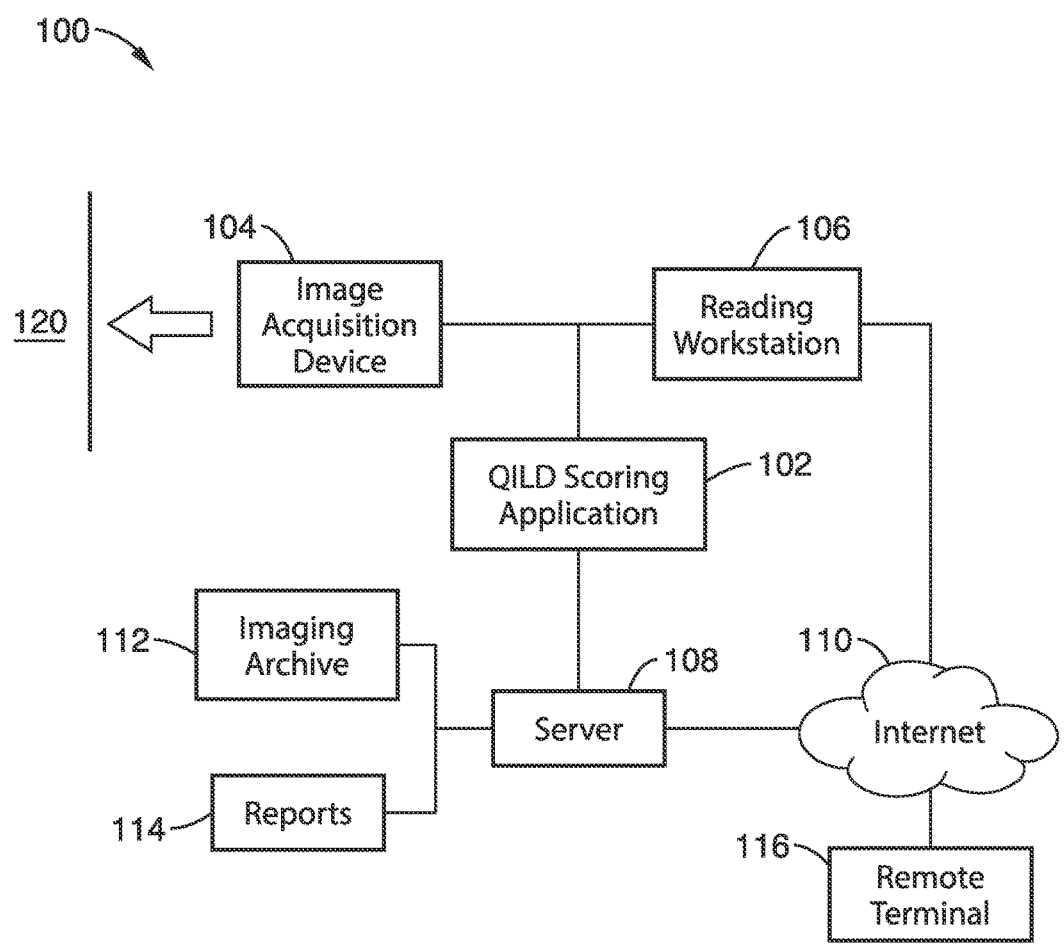
FIG. 3 is schematic diagram of an automated image system for scoring changes in Quantitative Interstitial Lung Disease (QILD) in accordance with the present invention.

FIG. 3 is a schematic diagram of an automated image system 100 for scoring changes in Quantitative Interstitial Lung Disease (QILD) in accordance with the present invention. In a preferred embodiment, system 100 is used to assess the change in a disease status of a patient in ILD, either in routine clinical practice or the setting of clinical trials. The method 10 of the present invention is preferably implemented as computer software, e.g. QILD scoring application 102. The scoring application 102 may be executable on the processor of an individual medical imaging workstation, either at the image acquisition device 104 (e.g. CT scanner generating images of patient 120) or on a reading workstation 106. The scoring application 102 may also be run on a centralized server 108 or cluster of servers in a radiology department or medical center. Running scoring application 102 on server 108 may offer some advantages in terms of interfacing with a centralized imaging archive 112 and storing reports 114 in a centralized database. The system 100 may also be accessed remotely via any terminal 116 coupled to the internet 110, for example, using GRID computing. Using this approach, the system 100 is made available as a GRID service and clients with proper authentication/authorization can access it world-wide.

8. Examples

Experiments were conducted to test the systems and methods of the present invention. Subjects had paired baseline and 12-month of DICOM (Digital Imaging and Communication in Medicine) Lung CT scans from the NIH sponsored trial of Scleroderma Lung Study (SLS) were used. They were treated with either Cyclophosphamide (CYC) or placebo. For all cases, the extent of the phenotype was measured via a Computer Aided Diagnosis (CAD) algorithm in accordance with the methods of the present invention. A Markov Chain Transition Matrix (MCTM) of the model was applied to the paired quantitative measurements for each subject to assess and measure the transition across the different disease phenotypes and the normal lung.

The descriptive statistics of MCTM for the imaging phenotypes is reported for the worst zone (upper, middle, or lower for each lung). Improvements in response to treatment are quantified below the diagonal of the MCTM. Similarly, worsening transitional patterns are indicated above the diagonal of the MCTM. Wilcoxon rank tests were used to compare CYC and placebo groups.

Figure 4A:
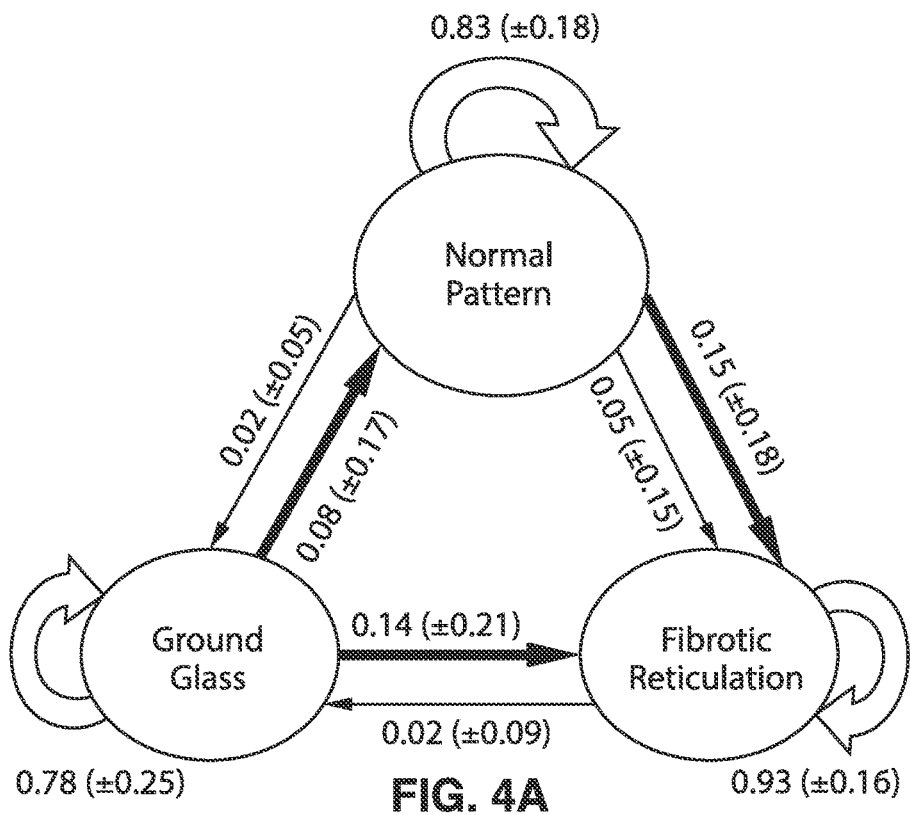
FIG. 4A and FIG. 4B show placebo group and CYC schema of a Markov chain transition matrix in accordance with the present invention.
Figure 4B:
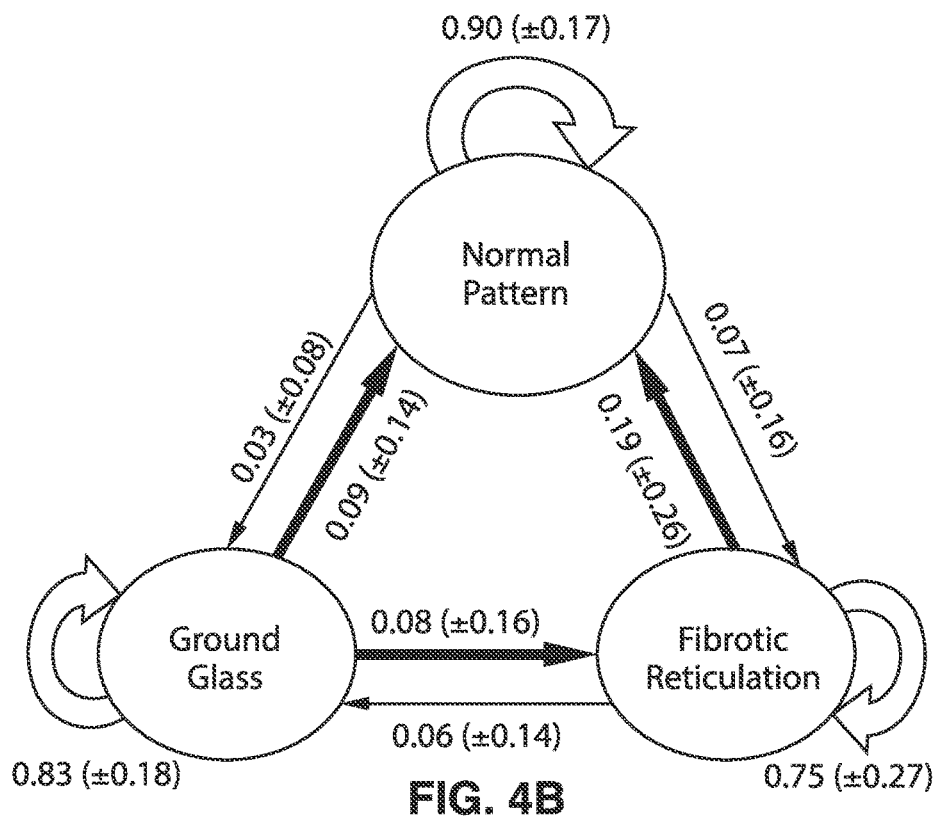

A MCTM was assessed in 83 subjects (N=42 in placebo and N=41 in CYC). No significant differences were found between CYC and placebo in the baseline characteristics. In CYC treated group, most changes occur on the diagonal and below of the transitional matrix, indicating stabilization and improvement. In the placebo group, the changes occur above the matrix diagonal, indicating progression. FIG. 4A and FIG. 4B show placebo group and CYC schema of the tested MCMT, respectively.

Figure 5:
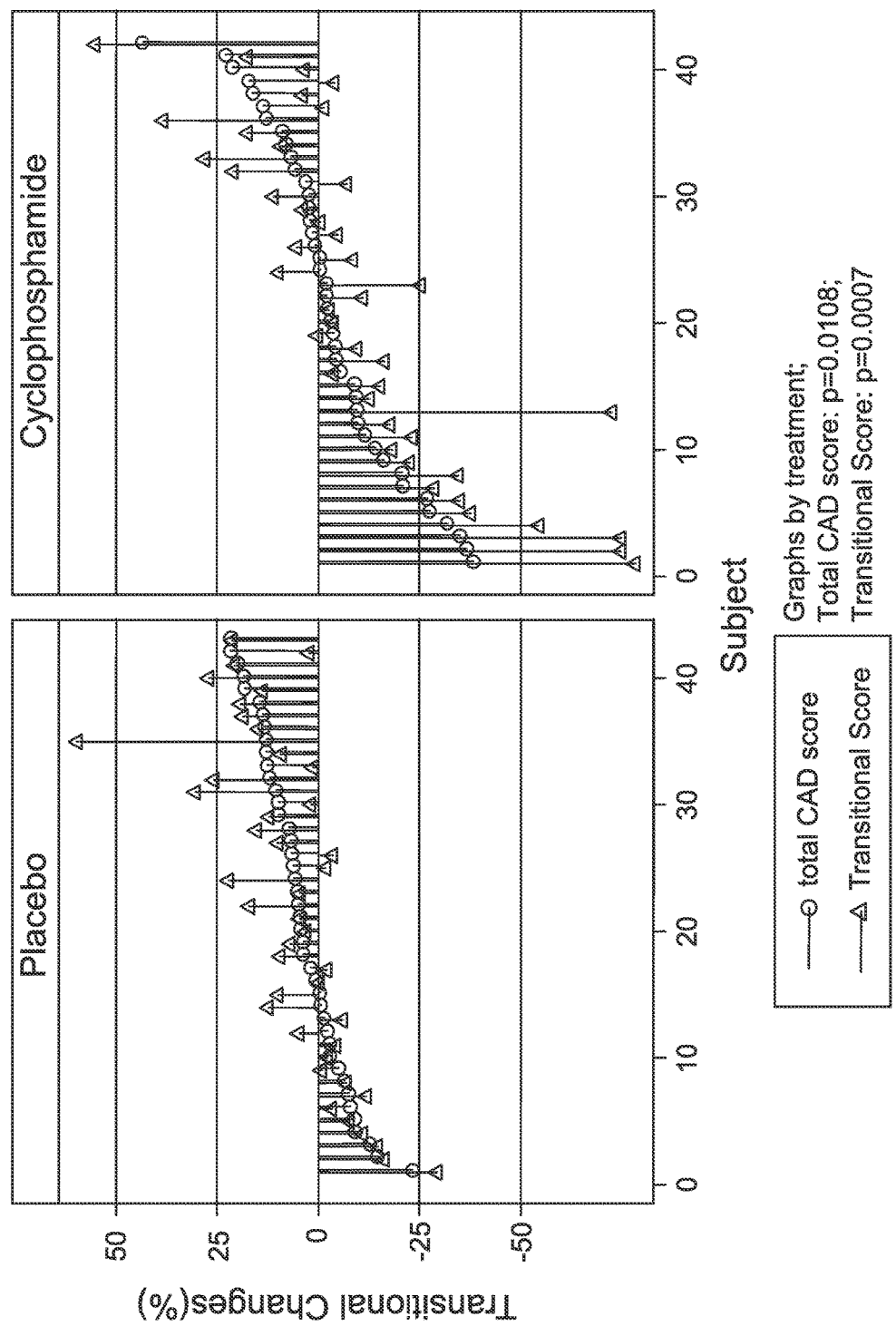
FIG. 5 shows drop-line plots for placebo and CYC changes in score at 12 months.

In the most severe zones identified at baseline, the transitional index changes are more pronounced with an 18% difference (p=0.0007) between two groups (11% reduction in CYC and 7% increase in placebo). FIG. 5 shows drop-line plots for placebo and CYC changes in score at 12 months.

In conclusion, the Markov Chain Transition Matrix (MCTM) ILD transitional index provides rich insights into multi-dimensional changes of remodeling or progression between the phenotypes beyond the individual changes. The systems and methods of the present invention are beneficial in assessing the quantitative changes in imaging phenotypes in response to therapy and offer insights into the mechanism of action.

The systems and methods of the present invention provide increased sensitivity and consistency over visual scoring. This has an advantage over standard methods, because it allows more rapid assessment of the treatment effects and shortening of clinical trials, so that drugs can be brought to a market at lower cost.

The methods of the present invention uniquely provide transitional overall changes of hierarchical severity in patterns illustrated using a Markov Chain. This provides a precise metric for determining treatment effects in a clinical trial or in clinical care. Using these new methods of evaluating fibrotic patterns and transitional scores in QILD, we are able to accurately evaluate treatment effects or progression of disease in interstitial lung disease.

The methods of the present invention also uniquely provide de-noising tools to allow for a reduction in image variation from multi-center trials. Quantitative scores may not be useful in a multi-center trial due to variations in image acquisition parameters and quality. The de-noising technique of the present invention can assist a radiologist to provide a more consistent quantitative scoring. From a clinical perspective, two types of fibrotic patterns were derived from the features from texture image: a fibrotic pattern indicating the early phase of fibrosis or a pattern of bronchiectasis.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A method for scoring changes in Quantitative Interstitial Lung Disease (QILD), comprising: uploading a plurality of CT images of a patient's lung; filtering the uploaded images to minimize cross-site variability within images; generating a QILD score for each image based on selected features within the image; and calculating a transition between QILD scores within the plurality of CT images.

2. A method as in any of the previous embodiments, further comprising: sampling from a grid of pixels or voxels within the CT images.

3. A method as in any of the previous embodiments, further comprising: classifying individual pixels or voxels within said downloaded images based on one or more selected texture features; and wherein the QILD score is calculated as the quotient of a total number of pixels or voxels within a CT image that are classified as a disease type by a total number (counts) of grid samples within the CT image.

4. A method as in any of the previous embodiments, wherein calculating a transition between QILD scores comprises calculating transitional changes of hierarchical severity within the image.

5. A method as in any of the previous embodiments, wherein the transitional changes of hierarchical severity are calculated using a Markov Chain.

6. A method as in any of the previous embodiments, wherein classifying individual pixels or voxels is a function of a classifier model built using Support Vector Machine (SVM). programming.

7. A method as in any of the previous embodiments, wherein the transition between QILD scores is used for estimating a transitional change in one or more of: fibrotic reticulation, ground glass and normal patterns associated with the patient's lung.

8. A method as in any of the previous embodiments, wherein calculating a transition between QILD scores comprises generating a Markov Chain Transition Matrix (MCTM) of the QILD scores.

9. A method as in any of the previous embodiments, wherein the MCTM is a function of the fibrotic reticulation, ground glass and normal patterns associated with the patient's lung.

10. A system for scoring changes in Quantitative Interstitial Lung Disease (QILD), comprising: a processor; and programming executable on said processor for: uploading a plurality of CT images of a patient's lung; filtering the uploaded images to minimize cross-site variability within images; generating a QILD score for each image based on selected features within the image; and calculating a transition between QILD scores within the plurality of CT images.

11. A system as in any of the previous embodiments, further comprising: sampling from a grid of pixels or voxels within the CT images.

12. A system as in any of the previous embodiments, said programming further configured for: classifying individual pixels or voxels within said downloaded images based on one or more selected texture features; and wherein the QILD score is calculated as the quotient of a total number of pixels or voxels within a CT image that are classified as a disease type by a total number (counts) of grid samples within the CT image.

13. A system as in any of the previous embodiments, wherein calculating a transition between QILD scores comprises calculating transitional changes of hierarchical severity within the image.

14. A system as in any of the previous embodiments, wherein the transitional changes of hierarchical severity are calculated using a Markov Chain.

15. A system as in any of the previous embodiments, wherein classifying individual pixels or voxels is a function of a classifier model built using Support Vector Machine (SVM) programming.

16. A system as in any of the previous embodiments, wherein the transition between QILD scores is used for estimating a transitional change in one or more of: fibrotic reticulation, ground glass and normal patterns associated with the patient's lung.

17. A system as in any of the previous embodiments, wherein calculating a transition between QILD scores comprises generating a Markov Chain Transition Matrix (MCTM) of the QILD scores.

18. A system as in any of the previous embodiments, wherein the MCTM is a function of the fibrotic reticulation, ground glass and normal patterns associated with the patient's lung.

19. A system for scoring changes in Quantitative Interstitial Lung Disease (QILD), comprising: a processor; and programming executable on said processor for: uploading a plurality of CT images of a patient's lung; filtering the uploaded images to minimize cross-site variability within images; sampling from a grid of pixels or voxels within the CT images; classifying individual pixels or voxels within said downloaded images based on one or more selected texture features; generating a QILD score for each image based on selected features within the image; wherein the QILD score is calculated as the quotient of a total number of pixels or voxels within a CT image that are classified as a disease type by a total number (counts) of grid samples within the CT image; and calculating a transition between QILD scores within the plurality of CT images.

20. A system as in any of the previous embodiments: wherein calculating a transition between QILD scores comprises calculating transitional changes of hierarchical severity within the image; and wherein the transitional changes of hierarchical severity are calculated by generating a Markov Chain Transition Matrix (MCTM) of the QILD scores.

21. A system as in any of the previous embodiments, wherein the MCTM is a function of the fibrotic reticulation, ground glass and normal patterns associated with the patient's lung.

22. A system as in any of the previous embodiments, wherein filtering comprises filtering noise as a function of geometric, texture, and noised images associated with the CT images.

23. A system as in any of the previous embodiments, wherein the classified disease types comprise one or more of: fibrotic reticulation, ground glass and normal patterns.

24. A system as in any of the previous embodiments, wherein the fibrotic reticulation disease type comprises is combined patterns of lung fibrosis and honeycomb.

25. A system as in any of the previous embodiments, wherein the QILD score is the sum of Quantitative Fibrotic Reticulation (QFR), Quantitative Ground Glass (QGG), and Quantitative Normal Lung (QNL) scores.

26. A system as in any of the previous embodiments, where the QFR score is the sum of quantitative lung fibrosis and honeycomb.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Features | Dimension |
|---|---|
| Statistical Features | Mean |
| | Standard Deviation |
| | Skewness |
| | Kurtosis |
| | Median |

TABLE 1-continued

| Features | Dimension |
|---|---|
| | Mode |
| | Mean32 |
| | Energy |
| | Entropy |
| | Ratio Highest |
| | Ratio Highest Lowest |
| Co-occurrence matrices 4 direction (0°, 45°, 90°, 135°), average, and range | Angular second moment |
| | contrast |
| | correlation |
| | difference entropy |
| | difference mean |
| | difference variance |
| | entropy |
| | inverse difference moment |
| | information measures of correlation-a |
| | information measures of correlation-b |
| | maximal correlation coefficient |
| | sum average |
| | sum entropy |
| | sum variance |
| | variance |
| Acquisition Length parameters 4 direction (0°, 45°, 90°, 135°), average, and range | short run emphasis |
| | long run emphasis |
| | low grey-level run emphasis |
| | high grey-level run emphasis |
| | short run low grey-level emphasis |
| | short run high grey-level emphasis |
| | long run low grey-level emphasis |
| | run length non-uniformity |
| | grey level non-uniformity |
| | run percentage |

TABLE 2

Training Set Of Classification Results

| | classification | | | |
|---|---|---|---|---|
| | Fibrotic Reticulation | GG | Normal* | Total |
| True class | | | | |
| FR | 3268 | 68 | 21 | 3357 |
| GG | 113 | 1762 | 119 | 1994 |
| Normal | 35 | 61 | 6234 | 6330 |

TABLE 3

Test Set Of Classification Results

| | classification | | | |
|---|---|---|---|---|
| | Fibrotic Reticulation | GG | Normal* | Total |
| True class | | | | |
| FR | 2812 | 64 | 80 | 2956 |
| GG | 169 | 1444 | 140 | 1753 |
| NL* | 72 | 112 | 5790 | 5974 |

TABLE 4

Classification Rates In The Training Set

| | Overall (FR, GG, NL) |
|---|---|
| Classification Rate (Sensitivity per type) | 96.4% (97.3%, 88.4%, 98.5%) |
| (Specificity per type) | (98.2%, 98.7%, 97.4%) |

TABLE 5

Classification Rates In The Test Set

| | Overall (FR, GG, NL) |
|---|---|
| Classification Rates (Sensitivity per type) | 94.0% (95.1%, 82.4%, 96.9%) |
| (Specificity per type) | (96.9%, 98.0%, 95.3%) |

TABLE 6

Markov Chain Transition Matrix (P) Per Subject's Lesion $\Delta QILD > 0$
P =

| $\Delta QGG > 0, \Delta QFR > 0$ | | | $\Delta QGG > 0, \Delta QFR \le 0$ | | | $\Delta QGG \le 0, \Delta QFR > 0$ | | |
|---|---|---|---|---|---|---|---|---|
| $\frac{QNL_2}{QNL_1}$ | $\frac{QGG_2 - QGG_1}{QNL_1}$ | $\frac{QFR_2 - QFR_1}{QNL_1}$ | $\frac{QNL_2}{QNL_1}$ | $\frac{QNL_1 - QNL_2}{NL_1}$ | 0 | $\frac{QNL_2}{QNL_1}$ | 0 | $\frac{QNL_1 - QNL_2}{QNL_1}$ |
| 0 | 1 | 0 | 0 | 1 | 0 | 0 | $\frac{QGG_2}{QGG_1}$ | $\frac{QGG_1 - QGG_2}{QGG_1}$ |
| 0 | 0 | 1 | 0 | $\frac{QFR_1 - QFR_2}{QFR_1}$ | $\frac{QFR_2}{QFR_1}$ | 0 | 0 | 1 |

$\Delta QILD \le 0$
P =

| $\Delta QGG \le 0, \Delta QFR \le 0$ | | | $\Delta QGG > 0, \Delta QFR \le 0$ | | | $\Delta QGG \le 0, \Delta QFR > 0$ | | |
|---|---|---|---|---|---|---|---|---|
| 1 | 0 | 0 | 1 | 0 | 0 | 1 | 0 | 0 |
| $\frac{QGG_1 - QGG_2}{QGG_1}$ | $\frac{QGG_2}{QGG_1}$ | 0 | 0 | 1 | 0 | $\frac{QNL_2 - QNL_1}{QGG_1}$ | $\frac{QGG_2}{QGG_1}$ | $\frac{QFR_2 - QFR_1}{QGG_1}$ |
| $\frac{QFR_1 - QFR_2}{QFR_1}$ | 0 | $\frac{QFR_2}{QFR_1}$ | $\frac{QNL_2 - QNL_1}{QRH_1}$ | $\frac{QGG_2 - QGG_1}{QRH_1}$ | $\frac{QFR_2}{QFR_1}$ | 0 | 0 | 1 |

What is claimed is:

1. A method for scoring changes in Quantitative Interstitial Lung Disease (QILD), comprising:
   uploading a plurality of CT images of a patient's lung;
   filtering the uploaded images to minimize cross-site variability within images;
   generating a QILD score for each image based on selected features within the image; and
   calculating a transition between QILD scores within the plurality of CT images.

2. A method as recited in claim 1, further comprising:
   sampling from a grid of pixels or voxels within the CT images.

3. A method as recited in claim 2, further comprising:
   classifying individual pixels or voxels within said downloaded images based on one or more selected texture features; and
   wherein the QILD score is calculated as the quotient of a total number of pixels or voxels within a CT image that are classified as a disease type by a total number (counts) of grid samples within the CT image.

4. A method as recited in claim 1, wherein calculating a transition between QILD scores comprises calculating transitional changes of hierarchical severity within the image.

5. A method as recited in claim 4, wherein the transitional changes of hierarchical severity are calculated using a Markov Chain.

6. A method as recited in claim 2, wherein classifying individual pixels or voxels is a function of a classifier model built using Support Vector Machine (SVM). programming.

7. A method as recited in claim 1, wherein the transition between QILD scores is used for estimating a transitional change in one or more of: fibrotic reticulation, ground glass and normal patterns associated with the patient's lung.

8. A method as recited in claim 1, wherein calculating a transition between QILD scores comprises generating a Markov Chain Transition Matrix (MCTM) of the QILD scores.

9. A method as recited in claim 8, wherein the MCTM is a function of the fibrotic reticulation, ground glass and normal patterns associated with the patient's lung.

10. A system for scoring changes in Quantitative Interstitial Lung Disease (QILD), comprising:
    a processor; and
    programming executable on said processor for:
        uploading a plurality of CT images of a patient's lung;
        filtering the uploaded images to minimize cross-site variability within images;
        generating a QILD score for each image based on selected features within the image; and
        calculating a transition between QILD scores within the plurality of CT images.

11. A system as recited in claim 10, further comprising:
    sampling from a grid of pixels or voxels within the CT images.

12. A system as recited in claim 11, said programming further configured for:
    classifying individual pixels or voxels within said downloaded images based on one or more selected texture features; and
    wherein the QILD score is calculated as the quotient of a total number of pixels or voxels within a CT image that are classified as a disease type by a total number (counts) of grid samples within the CT image.

13. A system as recited in claim 10, wherein calculating a transition between QILD scores comprises calculating transitional changes of hierarchical severity within the image.

14. A system as recited in claim 13, wherein the transitional changes of hierarchical severity are calculated using a Markov Chain.

15. A system as recited in claim 11, wherein classifying individual pixels or voxels is a function of a classifier model built using Support Vector Machine (SVM) programming.

16. A system as recited in claim 10, wherein the transition between QILD scores is used for estimating a transitional change in one or more of: fibrotic reticulation, ground glass and normal patterns associated with the patient's lung.

17. A system as recited in claim 10, wherein calculating a transition between QILD scores comprises generating a Markov Chain Transition Matrix (MCTM) of the QILD scores.

18. A system as recited in claim 17, wherein the MCTM is a function of the fibrotic reticulation, ground glass and normal patterns associated with the patient's lung.

19. A system for scoring changes in Quantitative Interstitial Lung Disease (QILD), comprising:
   a processor; and
   programming executable on said processor for:
      uploading a plurality of CT images of a patient's lung;
      filtering the uploaded images to minimize cross-site variability within images;
      sampling from a grid of pixels or voxels within the CT images;
      classifying individual pixels or voxels within said downloaded images based on one or more selected texture features;
      generating a QILD score for each image based on selected features within the image;
      wherein the QILD score is calculated as the quotient of a total number of pixels or voxels within a CT image that are classified as a disease type by a total number (counts) of grid samples within the CT image; and
      calculating a transition between QILD scores within the plurality of CT images.

20. A system as recited in claim 19:
   wherein calculating a transition between QILD scores comprises calculating transitional changes of hierarchical severity within the image; and
   wherein the transitional changes of hierarchical severity are calculated by generating a Markov Chain Transition Matrix (MCTM) of the QILD scores.

21. A system as recited in claim 20, wherein the MCTM is a function of the fibrotic reticulation, ground glass and normal patterns associated with the patient's lung.

22. A system as recited in claim 19, wherein filtering comprises filtering noise as a function of geometric, texture, and noised images associated with the CT images.

23. A system as recited in claim 19, wherein the classified disease types comprise one or more of: fibrotic reticulation, ground glass and normal patterns.

24. A system as recited in claim 23, wherein the fibrotic reticulation disease type comprises is combined patterns of lung fibrosis and honeycomb.

25. A system as recited in claim 19, wherein the QILD score is the sum of Quantitative Fibrotic Reticulation (QFR), Quantitative Ground Glass (QGG), and Quantitative Normal Lung (QNL) scores.

26. A system as recited in claim 25, where the QFR score is the sum of quantitative lung fibrosis and honeycomb.

* * * * *